United States Patent [19]

Haker

[11] 4,119,292
[45] Oct. 10, 1978

[54] MOULD FOR MAKING AND HOLDING A WORKING MODEL OF A JAW IMPRESSION FOR THE MANUFACTURE OF DENTAL PROSTHESES

[76] Inventor: Gerd Haker, Holstenstrasse 73, 2000 Hamburg 50, Germany

[21] Appl. No.: 820,894

[22] Filed: Aug. 1, 1977

[30] Foreign Application Priority Data

Aug. 4, 1976 [DE] Fed. Rep. of Germany ... 7624528[U]

[51] Int. Cl.² .................. A61C 9/00; A61C 19/00; B29C 1/16
[52] U.S. Cl. .......................... 249/54; 32/71; 425/175
[58] Field of Search ............ 249/DIG. 1, 54; 425/175; 32/32, 71

[56] References Cited

U.S. PATENT DOCUMENTS

| | | | |
|---|---|---|---|
| 2,718,126 | 9/1955 | Ball | 249/54 |
| 3,458,936 | 8/1969 | Schulz et al. | 32/71 |

Primary Examiner—Francis S. Husar
Assistant Examiner—John S. Brown
Attorney, Agent, or Firm—Stevens, Davis, Miller & Mosher

[57] ABSTRACT

The invention provides a mould for making and holding a working model of a jaw impression for use in the manufacture of dental prostheses. The mould has removable retaining elements connected to it for holding the working model in the mould and an arched internal wall arranged at a distance from the outer wall of the mould. The mould base has ribs for retaining the working model arranged between the outer wall and the internal wall of the mould and a hollow projection with an easily rupturable floor extending into the interior of the mould.

10 Claims, 2 Drawing Figures

MOULD FOR MAKING AND HOLDING A WORKING MODEL OF A JAW IMPRESSION FOR THE MANUFACTURE OF DENTAL PROSTHESES

The invention relates to a mould for making and holding a working model of a jaw impression for the manufacture of dental prostheses.

In the current state of the art numerous types of mould of various construction and composition are known for holding working models for making dental prostheses. To make replacement teeth, an impression (negative) of the upper or lower jaw or both is made by the dentist, and this impression is sent to the dental technician to prepare the dental prosthesis. The dental technician makes a working model (positive) of plastic or similar material in a mould from the impression made by the dentist.

To remove the working model together with the mould base from the remainder of the mould, it is known to provide removable retention parts whereby the base and model can be released from the mould.

One known one-piece plastic mould for making and holding a working model of a jaw impression for use in the manufacture of dental prostheses is shown in U.S. Pat. No. 4,022,419 and has removable retaining elements connected to the mould to hold the working model in the mould, an arched internal wall arranged at a distance from the outer wall of the mould, and retaining ribs for the working model arranged between the outer wall and the internal wall. The base of the last-mentioned mould is provided with an inbuilt line of weakness which can be ruptured so that, after the retaining elements have been removed, the working model can be pressed upwards from the mould by hand. A disadvantage of a mould of this kind is that the working model can only be removed with difficulty and may be damaged because the mechanical pressure exerted by hand is exerted only on a relatively small area.

It has now been found surprisingly that, with moulds of the last-mentioned type in particular, it is possible evenly to remove the working model by providing means whereby compressed air or other gas under pressure can be applied to the inside of the mould after the retaining elements have been removed.

Accordingly the present invention provides a mould for the manufacture and receipt of a working model of a jaw impression for use in the manufacture of dental prostheses, which mould comprises a base having an outer side wall, an internal wall spaced from the outer side wall, retaining ribs for the working model arranged between the outer side wall and the internal wall and means having an easily rupturable floor whereby compressed gas can be introduced into the interior of the mould within the base area bounded by the internal wall, and includes retaining elements to hold the working model in the mould.

In the mould of the invention, the means including an easily rupturable floor is preferably a hollow projection with an easily rupturable floor extending into the interior of the mould. A compressed air nozzle or the like can be introduced into this hollow projection after the floor has been ruptured, and air can be introduced and distributed evenly within the interior mould space bounded by the internal wall so that the working model is evenly removed from the mould after the retaining elements have been removed.

In the mould of the invention the hollow projection may have any suitable shape, but is preferably cylindrical in shape or is the shape of a hollow truncated cone.

With this latter construction, a nozzle for supplying compressed gas having an end appropriately shaped as a truncated cone can easily be inserted into the hollow projection and retained by friction.

In larger moulds of the above type, it has been found that when compressed gas is introduced there is a tendency for the working model to lift slightly at the rear of the mould and this may impede the effective removal of the working model from the mould. To pevent this, a further, retaining wall can be provided located in the space bounded by the internal wall, and typically adjacent the rear wall of the mould.

This retaining wall, which extends upwards from the floor inside the interior area of the mould, allows build-up of the necessary distributed pressure on the inner face of the mould base to provide for effective removal of large working models from the mould.

This retaining wall may extend from one side of the internal wall to the opposite side of the internal wall and when viewed in plan preferably has an apex, the point of the apex being towards the front of the mould. By the provision of this retaining wall, as large a part of the internal floor of the mould as possible can be acted upon by the compressed gas. It has also the advantage of providing space for hollow projections in the floor of the mould which serve to connect a mould with an articulator.

An embodiment of the invention will now be described by way of example with reference to the accompanying drawings in which.

Figure 1:
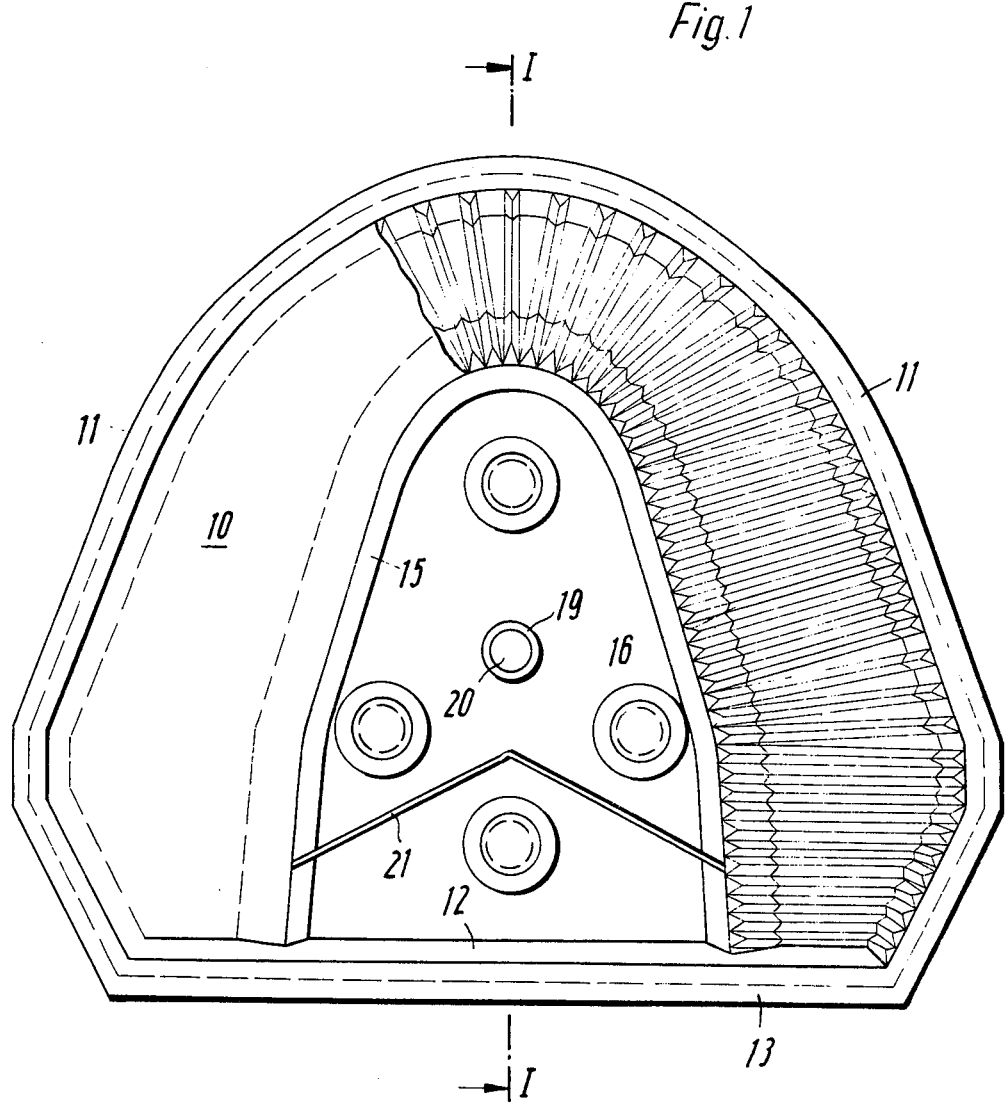
FIG. 1 shows a top plan view of a mould in accordance with the invention.

Referring to the drawings these show a mould generally denoted by the numeral 10 which has in plan and section a substantially U-shape, the shoulders of which broaden somewhat outwardly and then come together. The mould 10 has a side wall 11 and a rear wall 12. The side wall 11 extends upwardly and outwardly from the base 14 of the mould 10, as can be seen from FIG. 2. At their upper end the side wall 11 and the rear wall 12 are each provided with an outwardly directed circumferential guide flange 13. Under these flanges 13, the two retention elements (not shown) provided with upper horizontal flanges to extend over flanges 13 from above so as to hold the working model in the mould 10, can engage.

Figure 2:
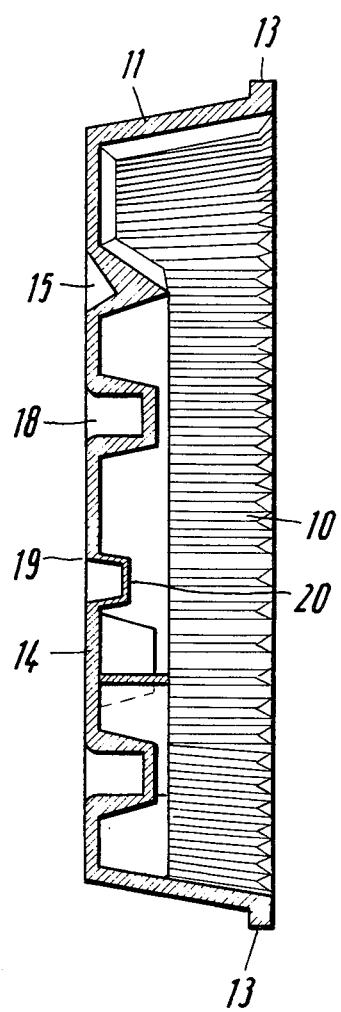
FIG. 2 shows a longitudinal section through the mould of FIG. 1 along line I—I.

Extending from the base 14 of the mould 10 and at a distance from the side wall 11 there is an internal wall 15 which has a height less than the height of the mould 10, as can be seen from FIG. 2. The side wall 11, part of the base 14, and one face of the wall 15 are provided on their surface with a plurality of small ribs 16, the cross-section of which diminishes outwardly from the floor or the walls. By means of this a plurality of grooves are formed into which the plaster can enter.

In the underside of the base 14 of the mould 10 bounded by the wall 15, several recesses 18 are provided, into which recesses parts of an articulator can engage. In the embodiment illustrated there are four such recesses 18 whose walls are formed in one piece with the base 14 of the mould 10.

A hollow projection 19 with an easily rupturable floor 20 is also provided in the base 14. Into this projection 19, after the floor has been ruptured, compressed air may be introduced by means of a suitable instrument, so that after the retaining elements have been released the working model, together with its base, can be pressed from the mould.

A retaining wall 21 is provided to the rear area of the space bounded by the wall 15 which prevents the working model from rising unintentionally on one side, when the retaining elements have been removed and compressed air or other gas under pressure is introduced. This retaining wall 21 ensures that within the inner area bounded by the wall 15 sufficient pressure builds up to press out large working models in large moulds.

According to one embodiment of the invention, the cross-section of this retaining wall 21 decreases from the base 14 upwards. This makes it easier for the working model to be lifted out when compressed air or other gas is used.

The retaining wall 21 is preferably formed with an apex and symmetrical to the centre line of the mould as shown so that, when compressed air is introduced into the space above the base of the mould, even pressure builds up in this space, ensuring that a working model therein will be pressed out without hindrance.

Before work is carried out, the retaining elements are attached to the mould 10 by means of their removable clasps in such a way that the elements are in a latched condition. The impression provided by the dentist and the mould 10 are then filled with plaster according to known techniques and, before the plaster has set, the plaster model is placed on the plaster in the mould 10 and the excess removed. After the plaster has set and hardened and after the clasps of the retaining elements have been released and the floor 20 of the hollow projection 19 punched through, the combination of working model and base is pressed out from the mould 10 in the manner described above. The working model with the base can then be sawn into as many parts as desired and the small elements of the model thus formed can be returned to the mould 10 and fixed by the retaining elements.

The mould or half-mould of the invention can be made of any suitable material, but is preferably made of polystyrene, which is comparatively inexpensive, for example by injection moulding. As a result of its one piece construction the mould can be made with the aid of a single divided tool. The retaining elements may be suitably likewise made of the same plastics in simple fashion.

I claim:

1. A mould for the manufacture and receipt of a working model of a jaw impression for use in the manufacture of dental prostheses, which mould comprises a base having an outer side wall, an internal wall spaced from the outer side wall, retaining ribs for the working model arranged between the outer side wall and the internal wall and a hollow projection in the mould base extending into the interior of the mould within the base area bounded by the internal wall, the projection having a floor which is easily reputable, and includes retaining elements to hold the working model in the mould.

2. A mould according to claim 1, wherein the hollow projection is cylindrical in shape.

3. A mould according to claim 1, wherein the hollow projection is in the shape of a truncated cone.

4. A mould according to claim 1, wherein there is a further, retaining wall located in the space bounded by the internal wall.

5. A mould according to claim 4, wherein the mould has a rear wall and the retaining wall is located adjacent the rear wall.

6. A mould according to claim 4, wherein the retaining wall extends from one side of the internal wall of the mould to an opposite side of the internal wall.

7. A mould according to claim 4, wherein the retaining wall, viewed in plan, has an apex.

8. A mould according to claim 4, wherein the retaining wall has the same height as the internal wall of the mould.

9. A mould according to claim 4, wherein the retaining wall is arranged symmetrical to the longitudinal axis of the area bounded by the internal wall.

10. A mould according to claim 4, wherein the retaining wall decreases in cross-section from the base upwards.

* * * * *